US00PP21095P2

(12) United States Plant Patent
Hofmann et al.

(10) Patent No.: US PP21,095 P2
(45) Date of Patent: Jun. 22, 2010

(54) ***NEMESIA* PLANT NAMED 'INNSUNMARA'**

(50) Latin Name: *Nemesia hybrida*
Varietal Denomination: Innsunmara

(75) Inventors: Silvia Hofmann, Gensingen (DE); Hendrik Theobald, Gensingen (DE)

(73) Assignee: InnovaPlant GmbH & Co. KG, Gensingen (DE)

( * ) Notice: Subject to any disclaimer, the term of this patent is extended or adjusted under 35 U.S.C. 154(b) by 0 days.

(21) Appl. No.: 12/315,572

(22) Filed: Dec. 3, 2008

(51) Int. Cl.
*A01H 5/00* (2006.01)

(52) U.S. Cl. ..... Plt./458

(58) Field of Classification Search ..... Plt./263, Plt./458
See application file for complete search history.

*Primary Examiner*—Susan B McCormick Ewoldt
(74) *Attorney, Agent, or Firm*—Mark P. Bourgeois

(57) ABSTRACT

A new cultivar of *Nemesia* plant named 'Innsunmara' that is characterized by large red orange flowers and good cold temperature tolerance.

1 Drawing Sheet

Botanical classification: *Nemesia hybrida.*
Variety denomination: 'Innsunmara'.

BACKGROUND OF THE INVENTION

The present invention relates to a new and distinct cultivar of *Nemesia* plant botanically known as *Nemesia hybrida* and hereinafter referred to by the cultivar name 'Innsunmara'.

The new *Nemesia* is the product of a planned breeding program conducted by the inventors in Gensingen, Germany. The objective of the breeding program is to create new *Nemesia* cultivars with unique colors and a compact habit.

'Innsunmara' is a hybrid that originated from a crossing in the Summer of 2003 of the female or seed parent a proprietary *Nemesia strumosa* identified as Neb Orange III (not patented) and the male or pollen parent a proprietary *Nemesia* identified as White Dream Typ I (not patented). The resulting seeds were subsequently planted and grown. The cultivar 'Innsunmara' was selected by the inventor in the Spring of 2004 as a single plant within the progeny of the stated cross in Gensingen, Germany.

Asexual reproduction of the new cultivar 'Innsunmara' first occurred by terminal cuttings in July of 2004 in Gensingen, Germany. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Nemesia* cultivar 'Innsunmara'. These traits in combination distinguish 'Innsunmara' as a new and distinct cultivar apart from other existing known varieties of *Nemesia.*

1. *Nemesia* 'Innsunmara' exhibits good cold temperature tolerance.
2. *Nemesia* 'Innsunmara' exhibits red orange flowers.
3. *Nemesia* 'Innsunmara' exhibits large flowers.

The closest comparison cultivar is *Nemesia* 'Kumquat' (not patented). 'Innsunmara' is distinguishable from 'Innsuncran' by the following characteristics:

1. 'Innsunmara' has red orange flowers. The flowers of 'Kumquat' are yellow orange.

2. 'Innsunmara' exhibits larger flowers than 'Kumquat'.
3. 'Innsunmara' has better cold temperature tolerance than 'Kumquat'.

BRIEF DESCRIPTION OF THE DRAWING

The accompanying photograph illustrates the distinguishing traits of *Nemesia* 'Innsunmara'.

The plant in the photograph shows an overall view of an 8 week old plant.

The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Nemesia* cultivar named 'Innsunmara'. Data was collected in Gensingen, Germany from 10 week old glass greenhouse grown plants in 12 cm. diameter containers. The time of year was autumn and the temperature range was 12–15 degrees Centigrade during the day and 8–10 degrees Centigrade at night. The light level was natural light. No photoperiodic treatments or growth retards were used. Color determinations are in accordance with The Royal Horticultural Society Colour Chart 2007 edition, except where general color terms of ordinary dictionary significance are used. The growing requirements are similar to the species. 'Innsunmara' has not been tested under all possible conditions and phenotypic differences may be observed with variations in environmental, climatic, and cultural conditions, however, without any variance in genotype.

Botanical classification: *Nemesia hybrida* 'Innsunmara'.

Annual or perennial: Annual.

Parentage: 'Innsunmara' is the product of the female or seed parent a *Nemesia strumosa* identified as Neb Orange III and the male or pollen parent a *Nemesia* identified as White Dream Typ I.

Vigor: Strong.

Growth habit: Prostrate, bushy.

Plant shape: Spreading, bushy.

Suitable container size: 12 cm. pots.
Height: 20 cm. in height.
Width: 18 cm. in width.
Low temperature tolerance: 0° Centigrade.
High temperature tolerance: 35° Centigrade.
Propagation: Leaf cuttings.
Time to initiate roots in summer: 10 to 12 days to initiate roots at 16 to 18° Centigrade.
Time to initiate roots in winter: 16 days to initiate roots at 16° Centigrade.
Time to produce a rooted cutting or liner in summer: 10 to 12 days at 16 to 18° Centigrade.
Time to produce a rooted cutting or liner in winter: 18 to 20 days at 16° Centigrade.
Crop time: Approximately 6 to 8 weeks.
Root system: Fine and fibrous, 20 to 30 cm. in diameter.
Stem:
*Branching habit.*—Lateral branches grow from every non-flowering axil.
*Basal branching.*—Yes.
*Average number of lateral branches.*—5.
*Pinching.*—Yes.
*Lateral branch diameter.*—4 mm. in diameter.
*Lateral branch length.*—12 to 25 cm. in length.
*Internode length.*—15 to 25 mm.
*Stem shape.*—Square with ridges at the corners.
*Stem strength.*—Moderate.
*Stem color.*—138B.
*Pubescence.*—Absent.
Foliage:
*Leaf arrangement.*—Opposite, petiolate.
*Compound or single.*—Single.
*Number of leaves per lateral branch.*—4 to 10.
*Leaf shape.*—Lanceolate.
*Leaf apex.*—Acuminate.
*Leaf base.*—Attenuate.
*Leaf length.*—5 to 8 cm. in length.
*Leaf width.*—2 to 3 cm. in width.
*Texture.*—Glabrous (upper and lower surfaces).
*Pubescence.*—None.
*Leaf margin.*—Dentate.
*Venation pattern.*—Simple.
*Young leaf color* (*upper surface*).—N137B.
*Young leaf color* (*lower surface*).—138B.
*Mature leaf color* (*upper surface*).—N137A.
*Mature leaf color* (*lower surface*).—138B.
*Vein color* (*upper surface*).—144A.
*Vein color* (*under surface*).—144B.
*Leaf attachment.*—Petiolate.
*Petiole dimensions.*—15 to 20 mm. in length, and 4 to 5 mm. in diameter.
*Petiole color.*—144B.
*Durability of foliage to stress.*—Moderate.
Flower:
*Inflorescence arrangement.*—Solitary/opposite in leaf axils.
*Quantity of flowers per inflorescence.*—1.
*Flower type.*—Zygomorphic.
*Quantity of flowers per lateral stem.*—2 per leaf pair.
*Quantity of flower buds per lateral stem.*—2 per leaf pair.
*Quantity of flowers and buds per plant.*—Average 150.
*Natural flowering season.*—April to October.
*Time to flower.*—5 weeks.
*Rate of flower opening.*—Every 4 to 6 days.
*Fragrance.*—None.
*Flower bud length.*—2 to 3 mm.
*Flower bud diameter.*—1 to 2 cm. in diameter.
*Flower bud shape.*—Saccate.
*Bud color.*—N34A.
*Rate of bud opening.*—4 to 6 days.
*Flower aspect.*—Outward.
*Flower shape.*—Zygomorphic.
*Flower dimensions.*—20 to 25 mm. in diameter and 10 mm. in height.
*Flower longevity.*—5–6 days.
*Number of petals.*—5.
*Fused or unfused.*—Fused.
*Petal arrangement.*—Upper 3 petals fused, lower 2 petals fused with protruding lip.
*Petal shape.*—Cordate.
*Petal margin.*—Indented.
*Petal apex.*—Cuneate.
*Petal base.*—Attenuate.
*Petal length.*—15 mm.
*Petal width.*—10 mm.
*Petal color when opening* (*upper side*).—Upper petals 32A, lower petals 25C.
*Petal color when opening* (*under side*).—Upper petals N34B, lower petals N34B.
*Petal color fully opened* (*upper side*).—Upper petals 32A, lower petals 25C.
*Petal color fully opened* (*under side*).—Upper petals N34C, lower petals N34C.
*Petal lip color* (*lower petals*).—20B.
*Petal color fading to.*—Upper petals 32B, lower petals 25D.
*Self-cleaning or persistent.*—Self-cleaning.
Sepals:
*Sepal appearance.*—Ligulate, pubescent.
*Sepal arrangement.*—Curved.
*Number of sepals.*—Average 5.
*Sepal shape.*—Ligulate.
*Sepal margin.*—Pubescent.
*Sepal apex.*—Attenuate.
*Sepal base.*—Fused.
*Sepal dimensions.*—7 to 8 mm. in length and 1 to 2 mm. in width.
*Young sepal color* (*upper side*).—137A.
*Young sepal color* (*under side*).—137B.
*Mature sepal color* (*upper side*).—137A.
*Mature sepal color* (*under side*).—137B.
Calyx:
*Calyx shape.*—Stellar, fused at base.
*Calyx dimensions.*—7 mm. in diameter.
Pedicels:
*Pedicel length.*—25 to 30 mm.
*Pedicel diameter.*—1 mm.
*Pedicel angle.*—30 degrees from stem.
*Pedicel strength.*—Weak.
*Pedicel color.*—137B.
Reproduction organs:
*Stamen number.*—5, 3 visible.
*Anther shape.*—Oval.
*Anther size.*—0.5 mm.
*Anther color.*—10C.
*Amount of pollen.*—Moderate.
*Pollen color.*—10C.
*Pistil number.*—1.
*Pistil length.*—0.5 mm.
*Stigma shape.*—Dentate.
*Stigma color.*—155D.

*Style length.*—1 mm.
*Style color.*—155D.
*Ovary color.*—155D.
Fruit: None, sterile triploid.
Disease and pest resistance: Disease and pest resistance has not been observed.

The invention claimed is:

1. A new and distinct variety of *Nemesia* plant named 'Innsunmara' as described and illustrated.

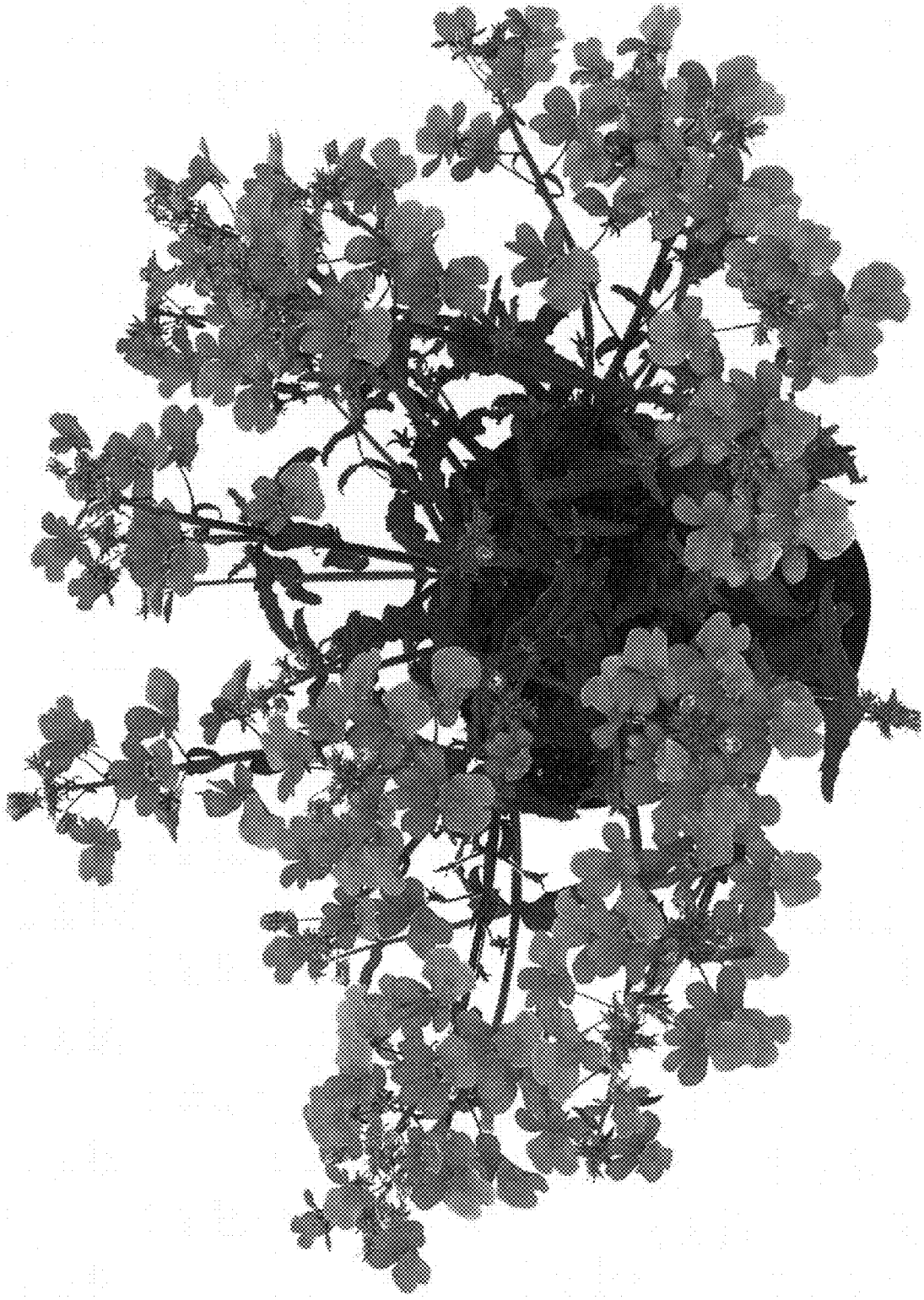

* * * * *